(12) United States Patent
Mattes et al.

(10) Patent No.: US 7,142,921 B2
(45) Date of Patent: Nov. 28, 2006

(54) SINGLE AXIS ACCELEROMETER AND METHOD THEREFORE

(75) Inventors: Michael F. Mattes, Chandler, AZ (US); Ralph B. Danzl, Tempe, AZ (US); Andreas A. Fenner, Chandler, AZ (US); Lary R. Larson, Gold Canyon, AZ (US)

(73) Assignee: Medtronic, Inc., Minneapolis, MN (US)

( * ) Notice: Subject to any disclaimer, the term of this patent is extended or adjusted under 35 U.S.C. 154(b) by 94 days.

(21) Appl. No.: 10/732,990

(22) Filed: Dec. 11, 2003

(65) Prior Publication Data

US 2005/0131482 A1    Jun. 16, 2005

(51) Int. Cl.
*A61N 1/362* (2006.01)

(52) U.S. Cl. ........................................ 607/19
(58) Field of Classification Search ................ 607/36, 607/5, 9, 17–25
See application file for complete search history.

(56) References Cited

U.S. PATENT DOCUMENTS 5,006,487 A    4/1991    Stokes
5,115,291 A    5/1992    Stokes
5,954,751 A *  9/1999    Chen et al. .................... 607/5

\* cited by examiner

*Primary Examiner*—Scott M. Getzow
(74) *Attorney, Agent, or Firm*—Michael C. Soldner; Carol F. Barry; Girma Wolde-Michael (57) ABSTRACT

Methods and apparatus are provided for an accelerometer. The apparatus includes first, second, and third substrates. The first substrate includes the first plate of a first capacitor. The second substrate includes a moveable mass that is coupled to the second substrate by at least one spring. The moveable mass is the second plate of the first capacitor and the first plate of a second capacitor. The third substrate includes the second plate of the second capacitor. The moveable mass is prevented from moving in any direction where the at least one spring is inelastically flexed. The first substrate couples to the second substrate. The third substrate couples to the second substrate. The method includes forming a moveable mass in a substrate. The moveable mass is formed having a plurality of springs coupling the moveable mass to the substrate. The moveable mass is released using a dry etch.

29 Claims, 11 Drawing Sheets

SINGLE AXIS ACCELEROMETER AND METHOD THEREFORE

TECHNICAL FIELD OF THE INVENTION

The present invention generally relates to micromachined structures, and more particularly relates to a single axis accelerometer for use in a medical device.

BACKGROUND OF THE INVENTION

A pulse generator is one of many medical devices that are implantable in a patient and provide a therapy that is dependent on the current status of the patient. For example, a pacemaker is a widely used medical device that includes a pulse generator for providing stimulus to cardiac tissue. The amount of stimulus provided corresponds to the activity level of the patient. A patient that is sleeping requires lower stimuli than a person that is active and in motion. One method for determining the status of the patient is to use an accelerometer.

An accelerometer measures changes in a patient's physical activity. The physical changes are detected by the accelerometer and algorithmically interpreted by circuitry within the pulse generator to produce a modified therapy that is correct for the current activity level. The accelerometer is placed within the implantable medical device. One type that has been successfully implemented in a pulse generator is a single axis accelerometer that measures both dynamic and static acceleration (e.g. gravity) in a single direction. Measurement in all three dimensions is achieved by using three single axis accelerometers respectively mounted to detect in the x, y, and z axis.

Figure 1:
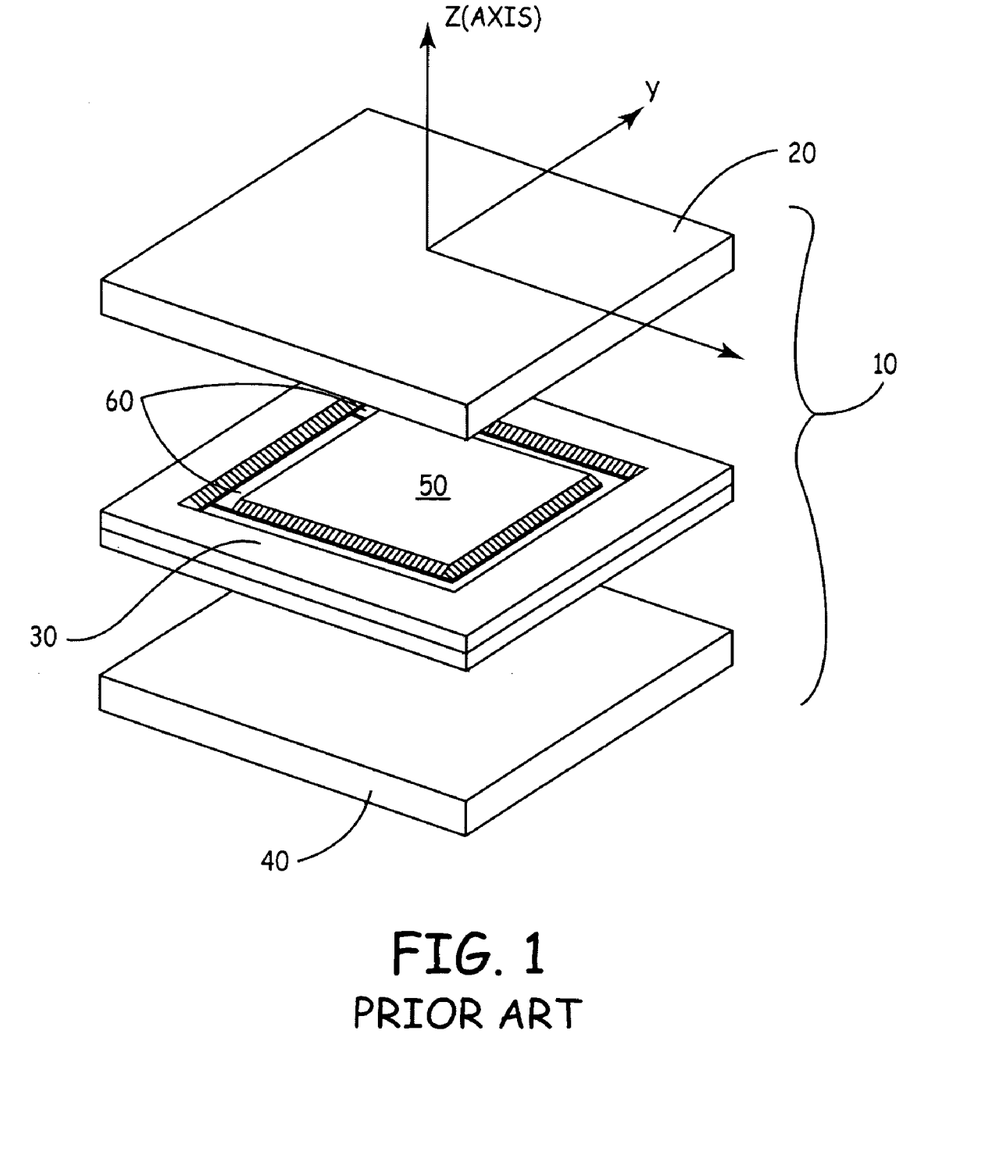
FIG. 1 is an isometric exploded view of a prior art accelerometer.

FIG. 1 is an isometric exploded view of a known accelerometer 10. Accelerometer 10 comprises a substrate 20, a substrate 30, and a substrate 40. In general, substrates 20, 30, and 40 are made of silicon. A moveable mass 50 is centrally located in substrate 30. The moveable mass is coupled to the main body of substrate 30 by flexures 60. For reference, the x, y, and z directions are shown relative to substrates 20, 30, and 40. Flextures 60 allow moveable mass 50 to move in the z-direction. A lower surface of substrate 20 couples to an upper surface of substrate 30. An upper surface of substrate 40 couples to a lower surface of substrate 30. Accelerometer 10 is sealed from an external environment when substrates 20, 30, and 40 are coupled together.

Moveable mass 50 is a conductive element. An upper surface of moveable mass 50 is spaced a predetermined distance from a conductive surface on the lower surface of substrate 20 forming a first capacitor. Similarly, a lower surface of moveable mass 50 is spaced a predetermined distance from a conductive surface on the upper surface of substrate 40 forming a second capacitor. The value of both the first and second capacitor changes as the moveable mass 50 moves. In an embodiment of accelerometer 10, the values of the first and second capacitors are used differentially such that the difference in capacitor values is detected. For example, moving mass 50 moves closer to the conductive surface on the lower surface of substrate 20 increasing the value of the first capacitor. Conversely, moveable mass 50 is moving farther away from the conducting surface of the upper surface of substrate 40 decreasing the value of the second capacitor. The difference between the first and second capacitors values is detected and corresponds to the movement induced in moving mass 50.

In general, moveable mass 50 is formed from the material comprising substrate 30. A wet etch is used to separate moveable mass 50 from substrate 30. The wet etch process leaves a substantial distance between moveable mass 50 and substrate 30. Flexures 60 are designed to flex which allows movement of moveable mass 50 in the z-direction. Flexures 60 are not flexible in the y-direction and may crack or fracture under conditions of high g-force in the y-direction. For example, dropping accelerometer 10 can produce movement in the y-direction where moveable mass 50 hits a sidewall of substrate 30. The distance between moveable mass 50 and the sidewall of substrate 30 is such that sufficient movement is generated to stress flexures 60 into cracking or fracturing.

Figure 2:
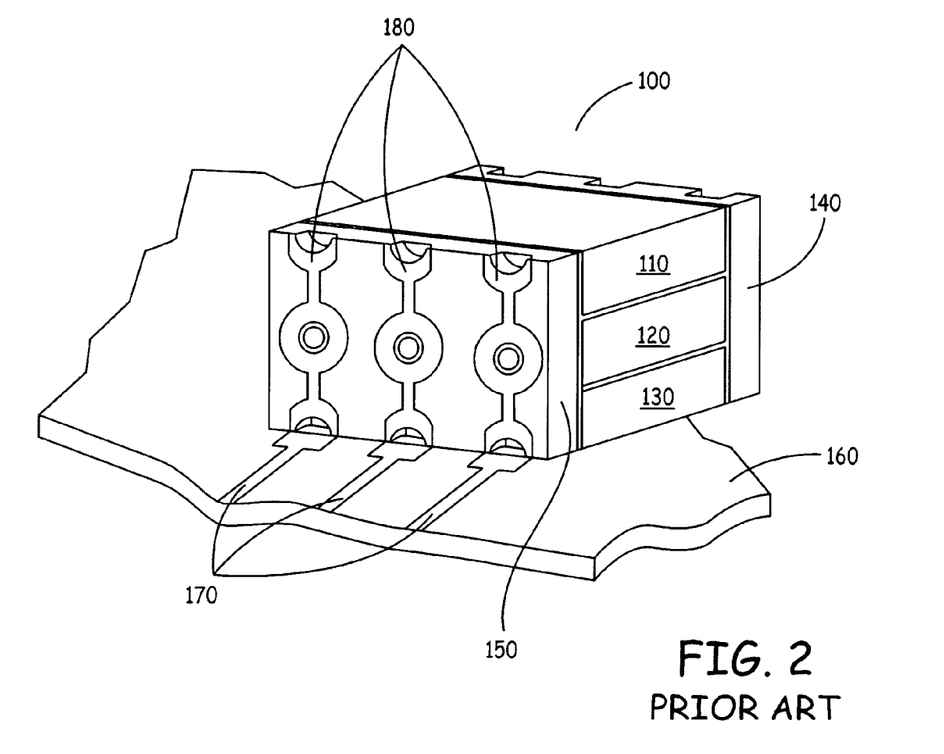
FIG. 2 is an isometric view of a prior art accelerometer coupled to a substrate.

FIG. 2 is an isometric view of a prior art accelerometer 100 coupled to a substrate 160. Accelerometer 100 includes substrates 110, 120, and 130 coupled together similar to that described in FIG. 1. An end cap 140 and an end cap 150 are coupled to substrates 110, 120, and 130. End caps 140 and 150 are primarily used for providing interconnection and physically fastening to substrate 160. Substrates 110, 120, and 130 have exposed interconnect (not shown) that abuts and couples to interconnect (not shown) on end cap 150. Interconnect 180 is coupled to the exposed interconnect (not shown) on substrates 110, 120, and 130. The three separate interconnects comprising interconnect 180 correspond to the terminals of two capacitors with one terminal common to both capacitors. The common terminal is the moveable mass in accelerometer 100.

End caps 140 and 150 increase the size, add complexity, and cost to the manufacture of accelerometer 100. Interconnect 180 aligns with and couples at a right angle to interconnect 170 on substrate 160. Solder or an adhesive epoxy is used to electrically couple interconnect 180 to interconnect 170. Although not shown, interconnect 170 typically couples to other circuitry (not shown) coupled to substrate 160.

Accordingly, it is desirable to provide a more reliable accelerometer. In addition, it is desirable to provide an accelerometer that is simple to manufacture and lower cost. It would be of further benefit if the accelerometer had a small footprint and was easily coupled to a substrate. Furthermore, other desirable features and characteristics of the present invention will become apparent from the subsequent detailed description and the appended claims, taken in conjunction with the accompanying drawings and the foregoing technical field and background.

BRIEF SUMMARY OF THE INVENTION

Methods and apparatus are provided for an accelerometer. The apparatus includes a first substrate, a second substrate, and a third substrate. The first substrate corresponds the first plate of a first capacitor. The second substrate is bonded to the first substrate. The second substrate includes a moveable mass that is coupled to the second substrate by at least one spring. The moveable mass corresponds to the second plate of the first capacitor and the first plate of a second capacitor. The third substrate is bonded to the second substrate. The third substrate corresponds to the second plate of the second capacitor. The moveable mass is prevented from moving in any direction that inelastically flexes the at least one spring. The method includes providing a first and third semiconductor substrate. A moveable mass is formed in a second semiconductor substrate. The moveable mass is formed having a plurality of springs coupling the moveable mass to the second semiconductor substrate. The moveable mass is released using a dry etch. The moveable mass is limited from moving in any direction that inelastically flexes the plurality of springs. The first semiconductor substrate is coupled to the second semiconductor substrate. The third semiconductor substrate is coupled to the second semiconductor substrate.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

Figure 3:
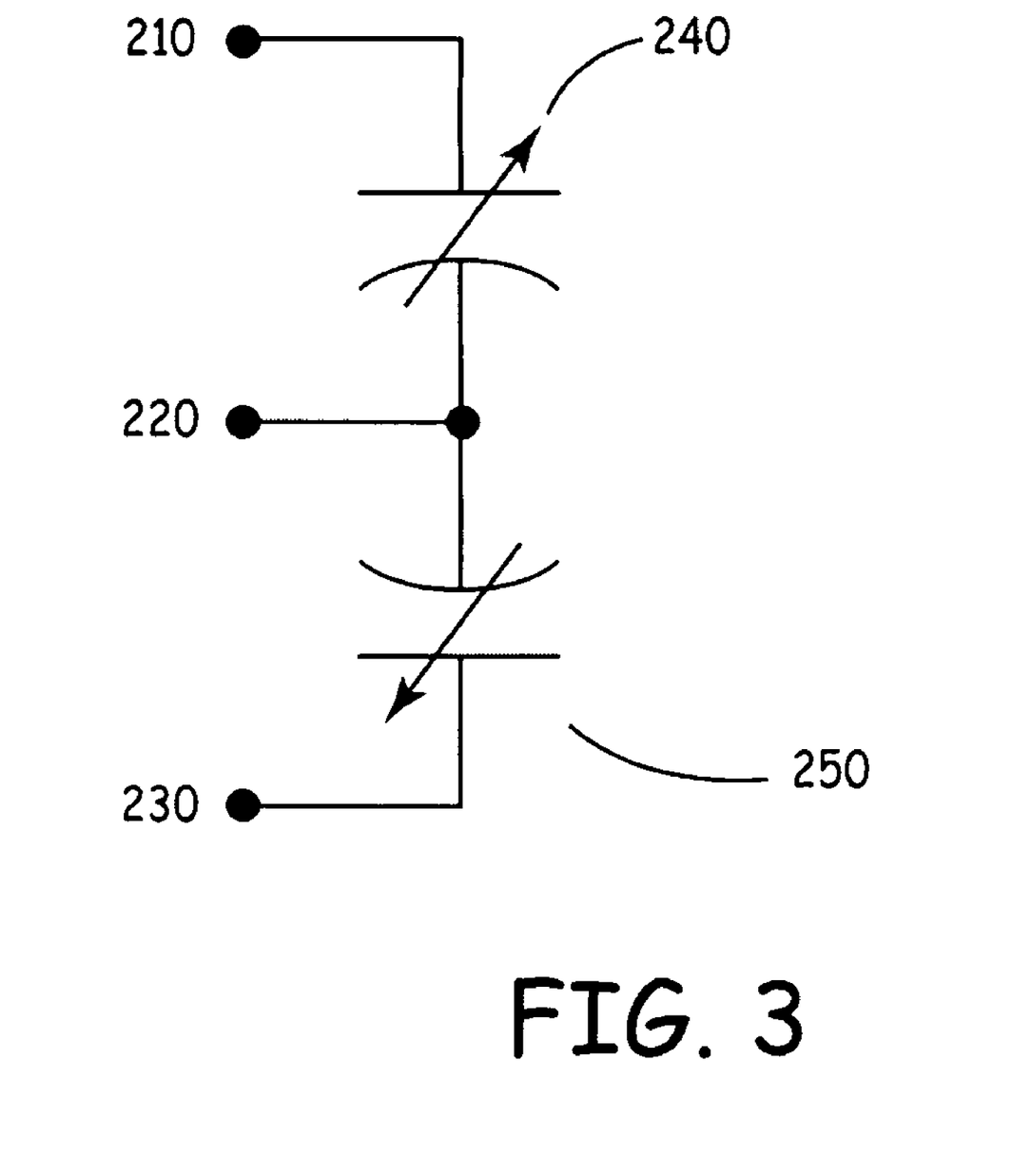
FIG. 3 is a schematic representation of an accelerometer in accordance with the present invention.

FIG. 3 is a schematic representation of an accelerometer in accordance with the present invention. The accelerometer is a three terminal device having a terminal 210, a terminal 220, and a terminal 230. The accelerometer includes a variable capacitor 240 and a variable capacitor 250. Capacitor 240 has a first capacitor plate coupled to terminal 210 and a second capacitor plate coupled to terminal 220. Capacitor 250 has a first capacitor plate coupled to terminal 220 and a second capacitor plate coupled to terminal 230.

In an embodiment of the accelerometer according to the present invention, the first capacitor plate of capacitor 240 and the second capacitor plate of capacitor 250 have a fixed position in the accelerometer. The second capacitor plate of capacitor 240 and the first capacitor plate of capacitor 250 are in common and together form a moveable mass within the accelerometer. The moveable mass is placed between the first capacitor plate of capacitor 240 and the second capacitor plate of capacitor 250 such that capacitors 240 and 250 have approximately the same capacitance under quiescent conditions. Movement of the accelerometer places the moveable mass closer to one of the fixed position capacitor plates and farther from the other thereby changing the capacitance value of capacitors 240 and 250. The change in capacitance is detectable and corresponds to the movement of the accelerometer.

An accelerometer is a micromachined element having moving parts. Shock can be imparted to the micromachined element before assembly and after the medical device is implanted in the patient. For example, it is possible for the medical device to be dropped by improper handling prior to implantation. The medical device would not have an outward signs of damage and could still work when enabled. The micromachined element could be stressed or fractured depending on the angle in which the medical device was dropped and the force of the shock. Moreover it is also not possible to look at the accelerometer and see any damage that may have occurred since it is a sealed device. This would be a long-term reliability problem for the medical device. The accelerometer described herein limits movement of the accelerometer to a distance where the springs elastically flex and do not reach a point where cracking or fracturing occurs.

Another factor that determines usability is the size of the accelerometer and how the device is assembled with other components of the medical device. The therapies being provided by implantable medical devices are becoming more complex. The complexity may include adding many outputs to the medical device. It is highly beneficial under this scenario to make the medical device as small as possible to allow placement near the targeted tissue where the therapy is provided. This allows the wiring size and length to be reduced as well as the miniaturization of any other delivery system required for the device. The accelerometer described herein minimizes the footprint and simplifies physical and electrical coupling to a substrate of the medical device.

Figure 4:
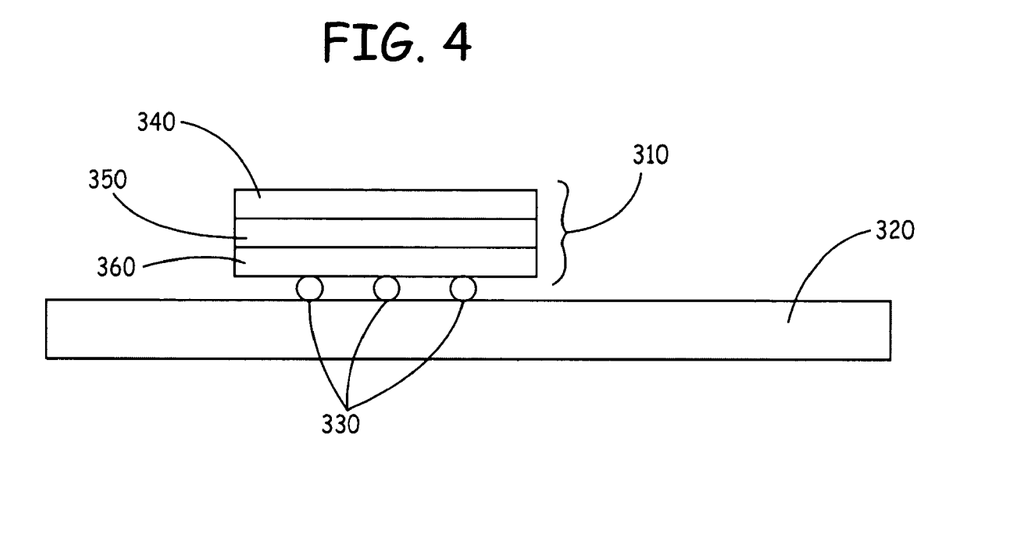
FIG. 4 is a side profile of an accelerometer coupled to a substrate in accordance with the present invention.

FIG. 4 is a side profile of an accelerometer 310 coupled to a substrate 320 in accordance with the present invention. Accelerometer 310 is a variable capacitor accelerometer having all electrical contact areas on a single major surface. In an embodiment of accelerometer 310, electrical contact areas are on a major surface of substrate 360. In general, each electrical contact area is a metal pad. The electrical contact areas correspond to the terminals of the variable capacitors. Accelerometer 310 includes substrates 340, 350, and 360 coupled together.

In one embodiment, accelerometer 310 is coupled to substrate 320 that is part of an implantable medical device. An example of an implantable medical device that may use accelerometer 310 is a pacemaker, defibrillator, or a pulse generator. Substrate 320 includes interconnect that couples to other circuits (not shown) of the medical device. Solder bumps 330 are formed on the electrical contact areas on substrate 360. Accelerometer 310 is placed such that solder bumps 330 align to, and contact corresponding electrical contact areas on substrate 360. The solder of solder bumps 330 is reflowed electrically and physically coupling accelerometer 310 to substrate 320. Flip chip mounting accelerometer 310 on substrate 320 allows a smaller implantable medical device to be made which is highly beneficial to the patient.

Figure 5:
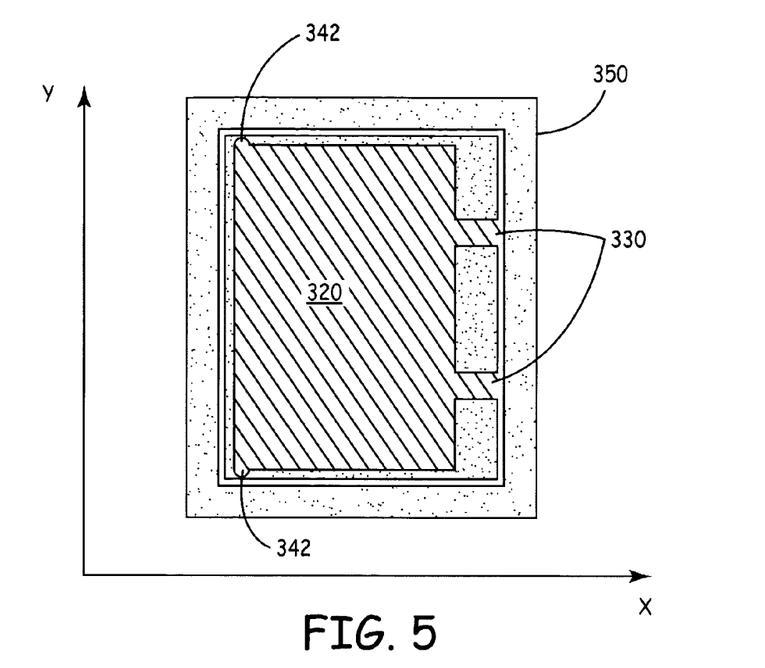
FIG. 5 is a top view of a middle substrate of an accelerometer in accordance with the present invention.

FIG. 5 is a top view of a middle substrate 350 of an accelerometer 310 corresponding to FIG. 4. Middle substrate 350 includes a moveable mass 320 supported by springs 330. Springs 330 allow moveable mass 320 to move in the z-direction. Springs 330 rigidly hold moveable mass 320 to prevent movement in the x and y direction. Mechanical failure of the accelerometer can occur if movement of moveable mass 320 stressed springs 330 to a point of fracture or cracking. An example of a shock that can stress springs 330 is dropping a component such as a medical device in which the accelerometer is used.

In this embodiment, movement of moveable mass 320 in the x-direction is not a substantial problem. Springs 330 have sufficient strength and are anchored securely to middle substrate 350 to prevent movement in the x-direction. Moveable mass 320 can move in the y-direction under some circumstances. Springs 330 will fracture if moveable mass 320 is allowed to move a sufficient distance in the y-direction. To prevent fracture under any conditions, the movement of moveable mass 320 is limited in the y-direction by over travel stops 342. Over travel stops 342 are formed on moveable mass 320 and extend outward to limit movement of moveable mass 320 in the y-direction. Over travel stops 342 come in contact with and engage against middle substrate 350 as moveable mass 320 moves in the y-direction, preventing further movement of moveable mass 320 in the y-direction. The amount of travel allowed in the y-direction is an amount that bends springs 330 elastically allowing springs 330 to return to their original position when normal operating conditions resume. Under normal operation of the accelerometer, over travel stops 342 are spaced away from middle substrate 350 and do not impair movement of moveable mass 320 in the z-direction.

Figure 6:
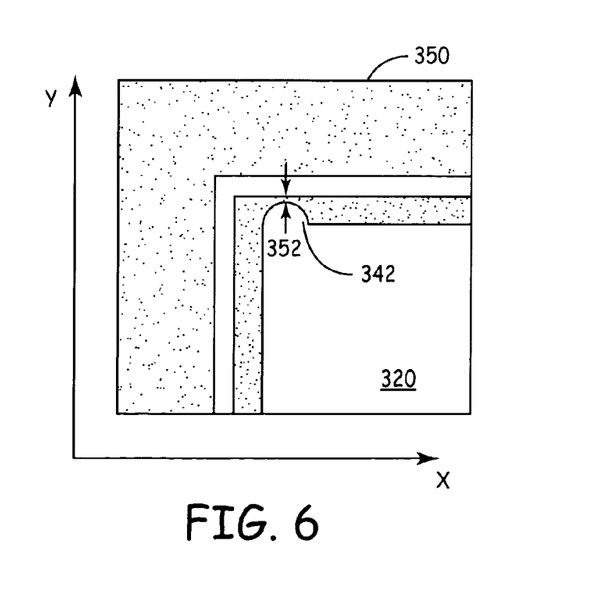
FIG. 6 is a magnified top view of an over travel stop in accordance with the present invention.

FIG. 6 is a magnified top view of an over travel stop 342 in accordance with the present invention. The magnified top view corresponds to the upper left corner of middle substrate 350 of FIG. 5. Over travel stop 342 is a semicircular shaped extension that extends outward from moveable mass 320 in the y-direction. A spacing 352 is the distance moveable mass 320 is allowed to travel in the y-direction before over travel stop 342 engages against middle substrate 310. As mentioned 5previously, spacing 352 is chosen to stress springs 330 elastically. Over travel stop 342 does not impede movement of moveable mass 320 in the z-direction.

Figure 7:
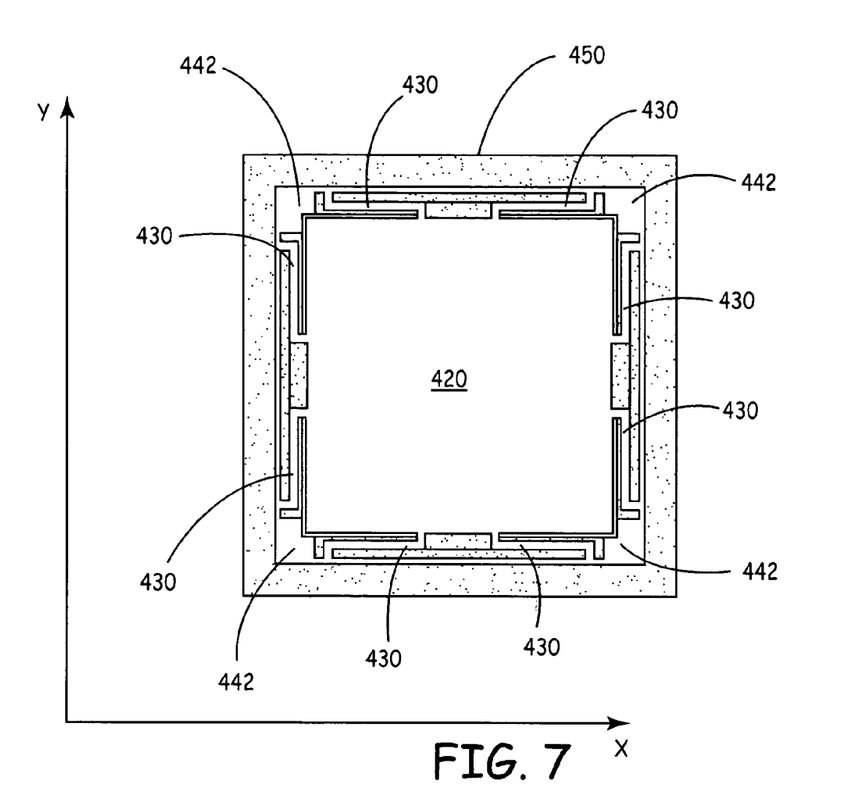
FIG. 7 is a top view of an alternate version of a middle substrate 410 in accordance with the present invention.

FIG. 7 is a top view of an alternate version of a middle substrate 450 in accordance with the present invention. A moveable mass 420 is coupled to middle substrate 450 by springs 430 in a manner similar to a trampoline. Moveable mass 420 moves in the z-direction and has two springs on each side. Over travel stops 442 are spaced a predetermined distance from moveable mass 420 and are formed in middle substrate 450. In an embodiment of middle substrate 450 according to the present invention, over travel stops 442 are placed in each corner of middle substrate 450 adjacent each corner of moveable mass 420 to prevent movement in the both the x and y direction. Over travel stops 442 limit movement in the x and y direction to a distance where springs 430 elastically flex and are prevented from fracturing. Under normal operating conditions, over travel stops 442 are not engaged against and therefore do not contact moveable mass 420.

Figure 8:
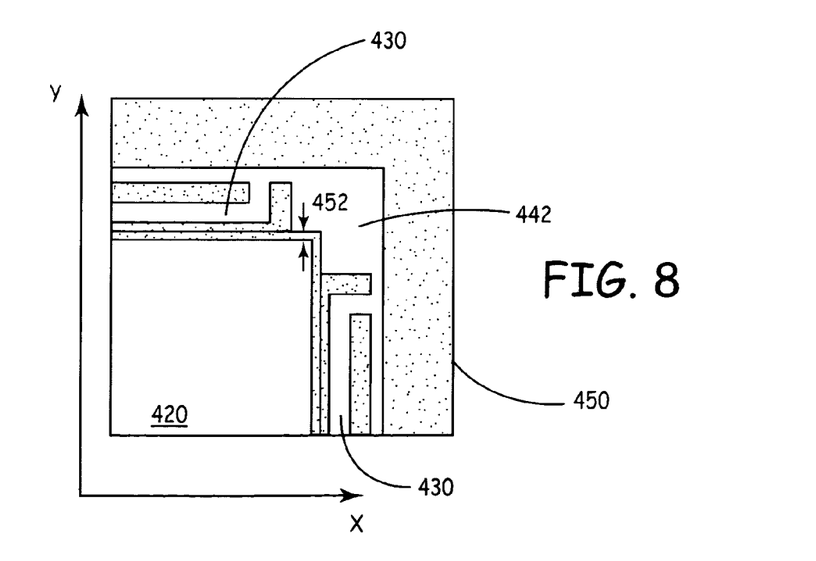
FIG. 8 is a magnified top view of an over travel stop for the alternate version of the middle substrate in accordance with the present invention.

FIG. 8 is a magnified top view of an over travel stop 442 in accordance with an embodiment of the present invention. The magnified view corresponds to the upper right corner of middle substrate 450 of FIG. 7. Over travel stop 442 is formed as a right angle corresponding to a corner of moveable mass 420. A spacing 452 is the distance moveable mass 420 is allowed to travel in the x or y-direction before moveable mass 420 contacts over travel stop 442. As mentioned previously, spacing 452 is chosen to stress springs 430 elastically. Over travel stop 440 does not 2impede movement of moveable mass 420 in the z-direction.

Figure 9:
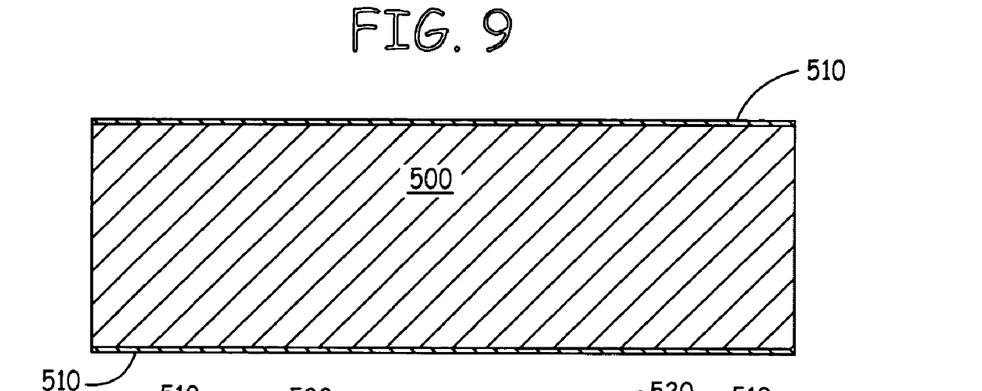
FIGS. 9–11 are cross-sectional views of a substrate illustrating wafer process steps to form a top cap of an accelerometer in accordance with the present invention.
Figure 10:
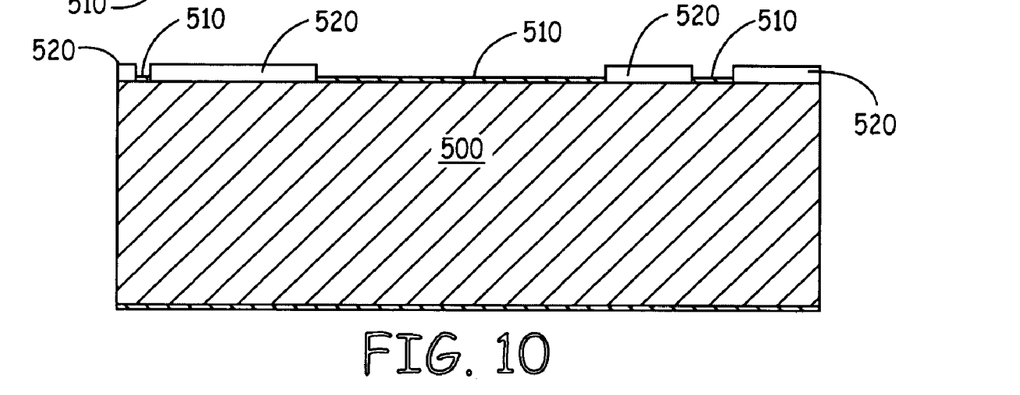
Figure 11:
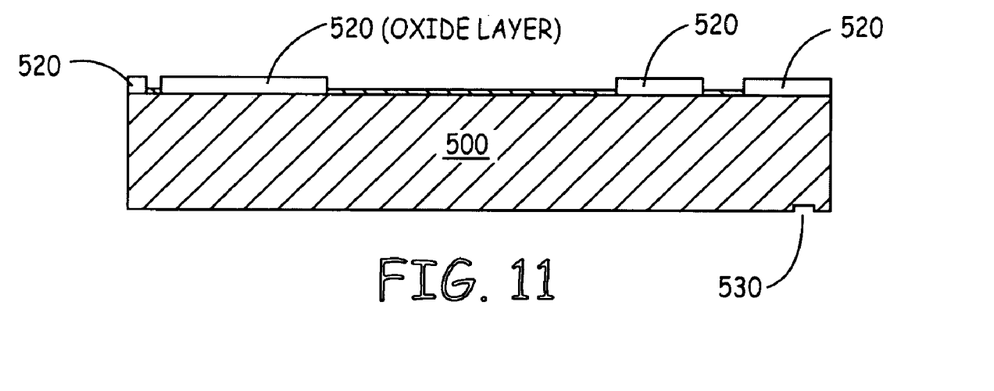

FIGS. 9–11 are cross-sectional views of a substrate illustrating wafer process steps to form a top cap of an accelerometer in accordance with an embodiment of the present invention. Substrate 500 is n-type silicon having a <100> crystal orientation. In an embodiment of the top cap according to the present invention, an oxide layer is first formed on substrate 500 followed by an overlying silicon nitride layer. The combination of the oxide layer and the silicon nitride layer is denoted as oxide/nitride layer 510. Oxide/nitride layer 510 acts as a protective layer on both surfaces of substrate 500 for subsequent processing steps. In an embodiment of the wafer process flow, the oxide layer is formed approximately 300 angstroms thick and the silicon nitride layer is formed approximately 1200 angstroms thick.

Referring to FIG. 10, a layer of photoresist is formed and patterned on a first side of substrate 500 exposing portions of oxide/nitride layer 510 of FIG. 9. The exposed silicon nitride layer is removed revealing the underlying oxide layer. The oxide layer is then removed exposing substrate 500. An oxide layer 520 is then formed in areas where substrate 500 is exposed. In an embodiment of the wafer process flow, oxide layer 520 is approximately 8000 angstroms thick. Oxide/nitride layer 510 is a non-conductive layer. Oxide/nitride layer 510 prevents the moveable mass of the accelerometer from shorting to substrate 500 should contact occur.

Referring to FIG. 11, a wafer thinning process is applied to substrate 500.

Material is removed from a second side of substrate 500. The second side is a backside on which no wafer process steps have been performed. In an embodiment of the wafer process, substrate 500 is thinned to approximately 13 mils. Photoresist is then applied to the second side of substrate 500 and patterned to expose portion of the backside surface of substrate 500. An etch is then performed to remove material from the backside surface of substrate 500 forming a trench 530 which is used later for alignment.

FIGS. 12–15 are cross-sectional views of a substrate 600 illustrating wafer process steps to form a bottom cap of an accelerometer in accordance with the present invention. Substrate 600 is n-type silicon having a <100> crystal orientation. An oxide layer is first formed overlying substrate 600. A silicon nitride layer is then formed overlying the oxide layer. The combination of the oxide layer and the silicon nitride layer is denoted as oxide/nitride layer 615. In an embodiment of the wafer process flow, the oxide layer is formed approximately 300 angstroms thick and the silicon nitride layer is formed approximately 1200 angstroms thick.

Figure 12:
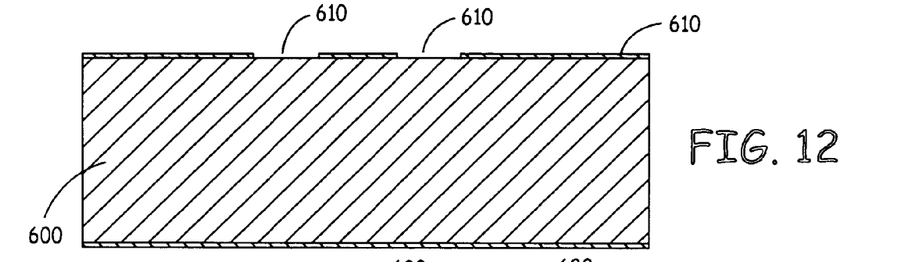
FIGS. 12–15 are cross-sectional views of a substrate illustrating wafer process steps to form a bottom cap of an accelerometer in accordance with the present invention.

Photoresist is then applied on the wafer and patterned exposing portions of the silicon nitride layer. The exposed silicon nitride layer is then removed revealing the underlying oxide layer. The exposed oxide layer is then removed revealing substrate 600. The area where substrate 600 is exposed is indicated by openings 610. The remaining photoresist is then removed.

Figure 13:
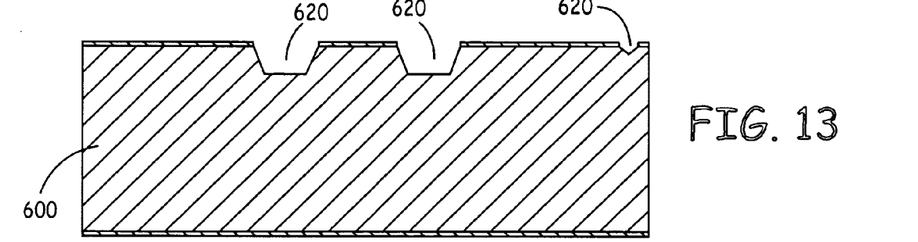

Referring to FIG. 13, an etch step is performed on substrate 600 in areas corresponding to openings 610 of FIG. 12. Trenches 620 are created by the silicon etch. In an embodiment of the wafer process, a TMAH etch is performed. The TMAH is a timed etch where the depth of trenches 620 corresponds to the size of opening 610 and the length of time of the etch. In an embodiment of the wafer process, the deeper trenches are formed to a depth of approximately 20 microns ±5 microns. The smaller trench will be used as an alignment aid in subsequent fabrication steps.

Figures 14, 15:
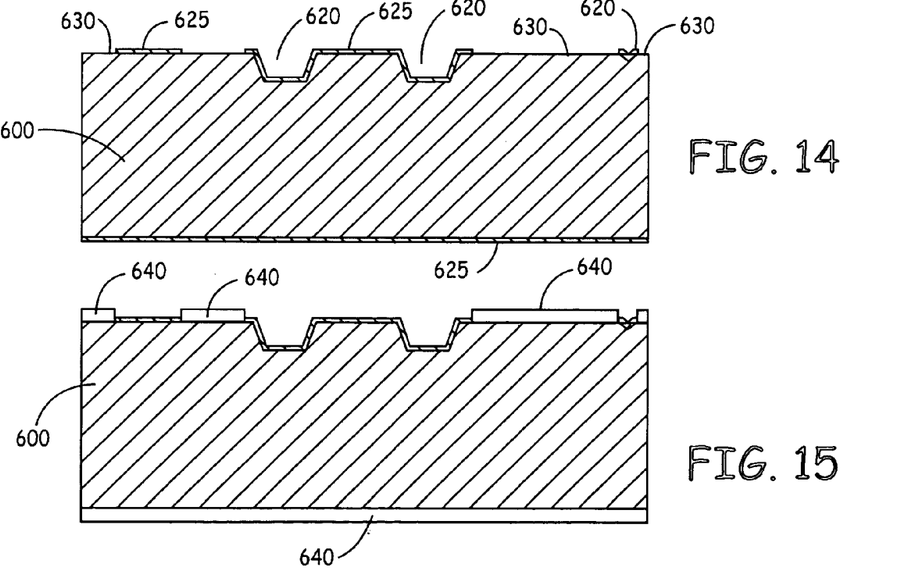
Figure 16:
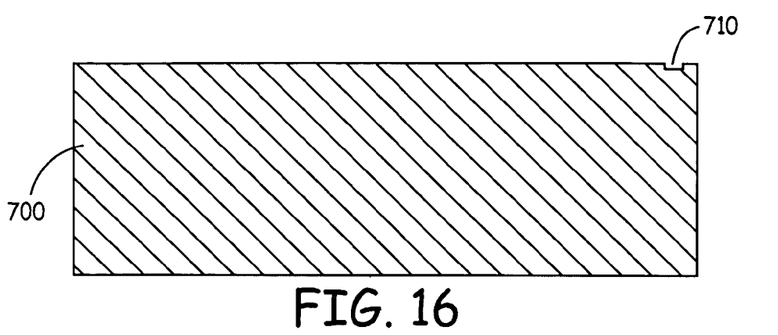
FIGS. 16–21 are cross-sectional views of a substrate illustrating wafer process steps to form a moveable mass of an accelerometer in accordance with the present invention.

Referring to FIG. 14, oxide/nitride layer 615 is removed from both surfaces of substrate 600. The first side of substrate 600 is the surface where trenches 620 of FIG. 13 are formed. After oxide/nitride layer 615 is removed, a new oxide layer is grown on both sides of substrate 600. A layer of silicon nitride is then formed overlying the layer of oxide on both sides of substrate 600. The combination of the oxide layer and the silicon nitride layer is denoted as oxide/nitride layer 625. In an embodiment of the wafer process, the layer of oxide is approximately 300 angstroms thick and the silicon nitride layer is approximately 1200 angstroms thick. Oxide/nitride layer 625 aligns with the moveable mass of the accelerometer is non-conductive thereby prevents shorting the moveable mass to substrate 600. A layer of photoresist is formed overlying the first side of substrate 600 and patterned exposing areas of the silicon nitride layer. The exposed silicon nitride is removed on both the first and second sides of substrate 600 revealing the underlying oxide layer. The oxide layer is then removed exposing areas of substrate 600 on the first side indicated by openings 630. The second side of substrate 600 is also exposed.

Referring to FIG. 15, an oxide layer 640 is grown in openings 630 of FIG. 14 and the backside of substrate 600. In an embodiment of the wafer process, oxide layer 630 is approximately 8000 angstroms thick.

FIGS. 16–21 are cross-sectional views of a substrate 700 illustrating wafer process steps to form a moveable mass of an accelerometer in accordance with the present invention. Substrate 700 is a middle substrate for the accelerometer. Photoresist is applied on a first side of the substrate 700 and patterned exposing a portion of substrate 100. The exposed portion of substrate 100 is etched forming a trench 710 that is used for alignment in subsequent steps.

Figure 17:
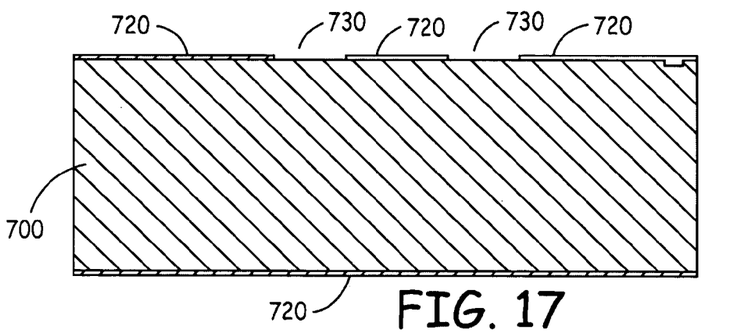

Referring to FIG. 17 a layer an oxide layer is formed on both sides of substrate 700. A silicon nitride layer is then formed overlying the oxide layer on both sides of substrate 700. In an embodiment of the wafer process, the oxide layer is approximately 300 angstroms thick and the silicon nitride layer is approximately 1200 angstroms thick. The combination of the oxide layer and the silicon nitride layer is indicated by oxide/nitride layer 720. Oxide/nitride layer 720 denotes the combination of the oxide layer and the silicon nitride layer.

Photoresist is applied on the first side of substrate 700 and patterned to expose areas of oxide/nitride layer 720. The exposed silicon nitride layer is removed revealing the underlying oxide layer. The exposed oxide layer is then removed revealing substrate 700. The exposed areas of substrate 700 are identified by openings 730. A p-implant is deposited into substrate 700 through openings 730. In an embodiment of the wafer process, a p-type material comprising BF2 @ 3E15, 60 KeV is implanted through openings 730. The p-implant is driven in to a depth of approximately 0.4 microns in a subsequent thermal cycle. The p-implant is an etch stop for a subsequent step of the wafer process.

Figure 18:
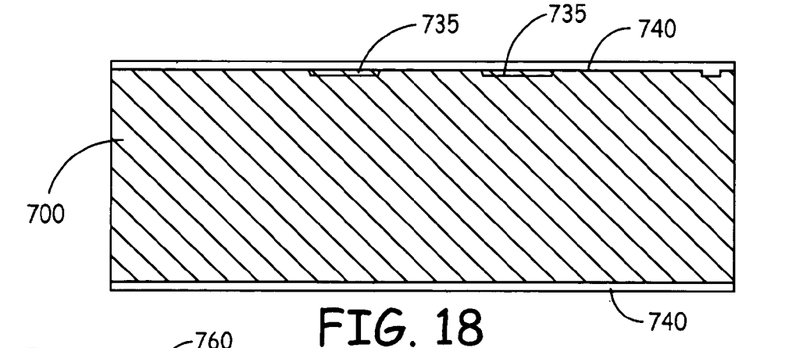

Referring to FIG. 18, the p-implants driven in substrate 700 as described in FIG. 17 are shown as p-wells 735. Oxide/nitride layer 720 of FIG. 17 is then removed from the first and second side of substrate 700. An oxide layer 740 is formed on both sides of substrate 700. In an embodiment of the wafer process, oxide layer is approximately 500 angstroms thick and is used to protect the wafer surface prior to forming an epitaxial layer.

Figure 19:
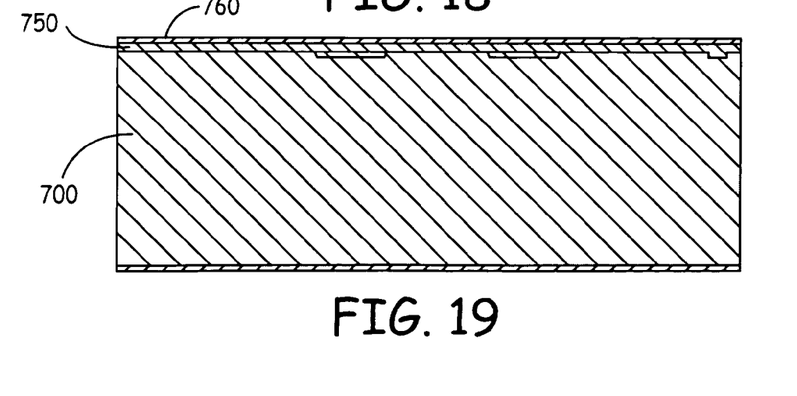

Referring to FIG. 19, oxide layer 740 of FIG. 18 is removed and an epitaxial layer 750 is formed on the first side of substrate 700. In an embodiment of the wafer process, epitaxial layer 750 is an n-type epitaxial layer and is formed having a thickness of approximately 20 microns. An oxide layer is then formed overlying epitaxial layer 750 and on the second side of substrate 700. A silicon nitride layer is then formed overlying the oxide layer on both sides of substrate 700. Oxide/nitride layer 760 denotes the combination of the oxide layer and the silicon nitride layer. In an embodiment of the wafer process, the oxide layer has a thickness of 300 angstroms and the silicon nitride layer has a thickness of 1200 angstroms.

Figure 20:
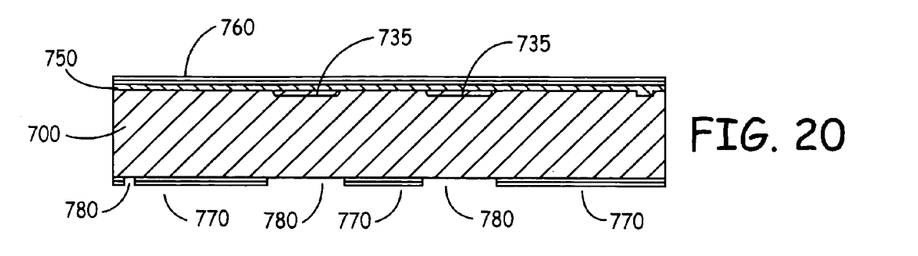

Referring to FIG. 20, a wafer thinning process is performed on the second side of substrate 700. In an embodiment of the wafer process, substrate 700 is thinned to approximately 13 mils thick.

An oxide layer is then formed on the second side of substrate 700. A silicon nitride layer is then formed overlying the oxide layer on the second side of substrate 700. Oxide/nitride layer 770 denotes a combination of the oxide layer and the silicon nitride layer. In an embodiment of the wafer process, the oxide layer is formed approximately 300 angstroms thick and the silicon nitride layer is formed approximately 1200 angstroms thick.

Photoresist is formed and patterned on the second side of substrate 700 exposing portions of oxide/nitride layer 770. In particular, the moveable mass of the accelerometer is being defined. The exposed silicon nitride layer is then removed on the second side of substrate 700 revealing the underlying oxide layer. The exposed oxide layer is then removed revealing substrate 700. The exposed areas of substrate 700 is denoted by openings 780. Some of openings 780 align with p-wells 735 on the first side of substrate 700.

Figure 21:
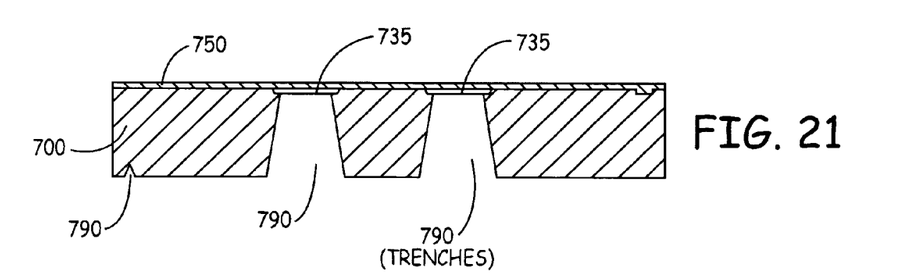

Referring to FIG. 21, an etch is performed to remove exposed silicon from the second side of substrate 700 through openings 780 of FIG. 20. The etch is terminated when p-wells 735 are reached. As mentioned previously, p-wells 735 act as an etch stop for this etch step. A substantial amount of substrate 700 is removed through openings 780 almost reaching the first side of substrate 700. In an embodiment of the wafer process, the etch is a TMAH etch. The etched areas are denoted as trenches 790. Oxide/nitride layer 760 and 770 of FIG. 20 are then removed respectively exposing the underlying epitaxial layer 750 and the second side of substrate 700.

Figure 22:
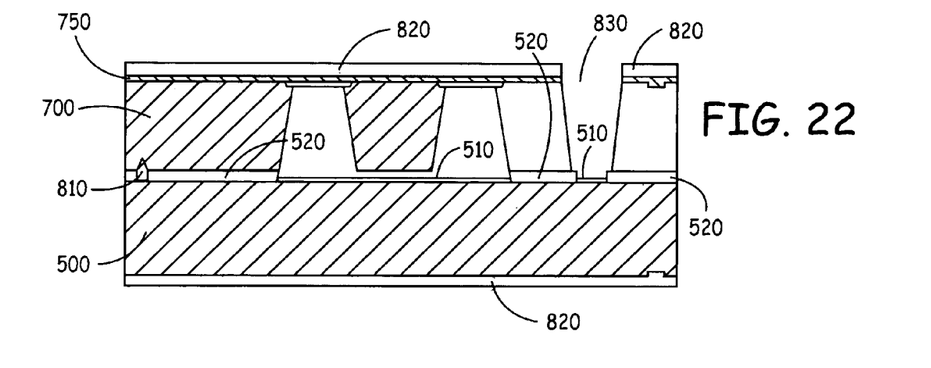
FIGS. 22–23 are cross-sectional views of a middle substrate coupled to top cap in accordance with the present invention.
Figure 23:
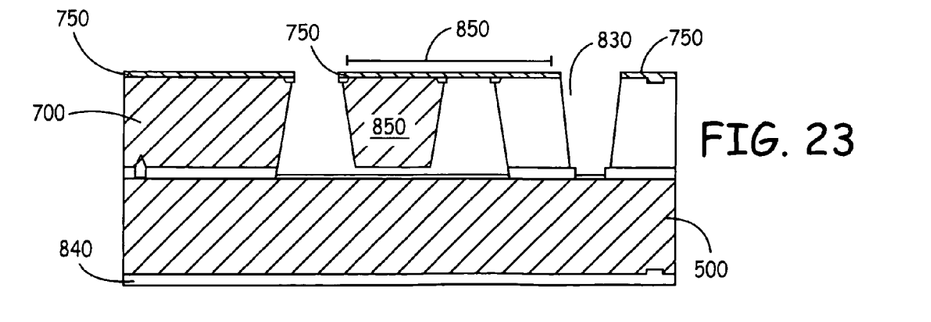

FIGS. 22–23 are cross-sectional views of a middle substrate coupled to a top cap in accordance with the present invention. The top cap and middle substrate respectively correspond to substrate 500 disclosed in FIGS. 9–11 and substrate 700 disclosed in FIGS. 16–21. Substrate 500 and substrate 700 are aligned to one another using target fields 810. The target fields 810 are trenches formed in the surface of each substrate during previous wafer processing steps when substrates 500 and 700 were individual wafer processed. In an embodiment of the wafer process, substrate 500 is coupled to substrate 700 in a fusion bond. Oxide layer 520 overlying substrate 500 is in contact with the surface of substrate 700. A heating step fuses oxide layer 520 to substrate 700 that permanently holds substrates 500 and 700 together.

An oxide layer 820 is formed overlying epitaxial layer 750. Oxide layer 820 is also formed overlying substrate 500. In an embodiment of the wafer process, oxide layer 820 is formed having a thickness of approximately 8000 angstroms. A photoresist layer is then formed overlying oxide layer 820 on substrate 700 and patterned. The photoresist layer is patterned to create a middle via. An exposed area of oxide layer 820 is removed by etching revealing the underlying epitaxial layer 750. The exposed epitaxial layer 750 and the underlying substrate 700 are then etched. In an embodiment of the wafer process, a TMAH etch is used to form the middle via. The etch stops upon reaching oxide/nitride layer 510 and oxide layer 520. A trench 830 is formed that couples through substrate 700.

Referring to FIG. 23, oxide layer 820 shown in FIG. 21 is removed from substrate 500 and substrate 700. An oxide layer 840 is then formed overlying substrate 500 and substrate 700. In an embodiment of the wafer process oxide, layer 840 is a dielectric oxide approximately 400–500 angstroms thick. Oxide layer 840 also overlies an exposed surface of substrate 700 in trench 830.

Photoresist is formed on substrate 700 and patterned to release a moveable mass 850. The pattern includes over travel stops (not shown) to limit movement of moveable mass 850. Exposed areas of oxide layer 840 are then etched to reveal the underlying epitaxial layer 750. Spacing between moveable mass 850 and substrate 700, and more particularly to the over travel stops is important. A dry etch is used to etch exposed areas of epitaxial layer 750, and the underlying p-wells 735 of FIG. 21 which releases moveable mass 850. Epitaxial layer 750 coupling moveable mass 850 to substrate 700 forms springs 860. The dry etch controls spacing between moveable mass 850 and substrate 700 that limits movement of moveable mass 850 to a distance where springs 860 flex elastically to movement in all directions thereby preventing fracturing of springs 860 under a high shock condition. In other words, moveable mass 850 cannot move in a manner that would inelastically flex springs 860 and damage the accelerometer. Oxide layer 840 overlying substrate 700 is then removed.

Figure 24:
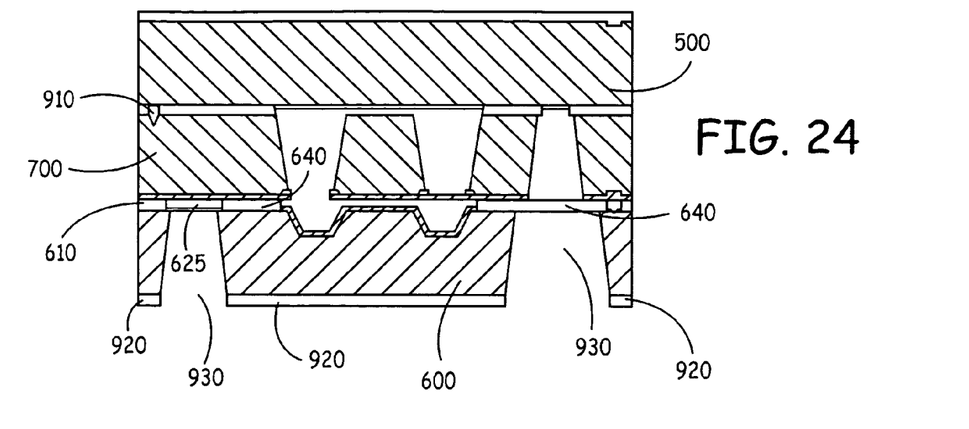
FIGS. 24–26 are cross-sectional views of a top cap, middle substrate, and a bottom cap coupled together in accordance with the present invention.
Figure 25:
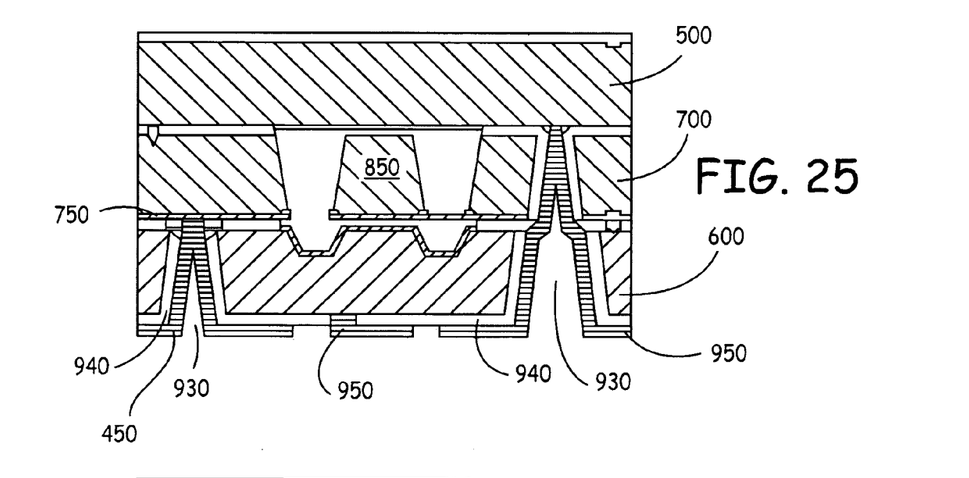
Figure 26:
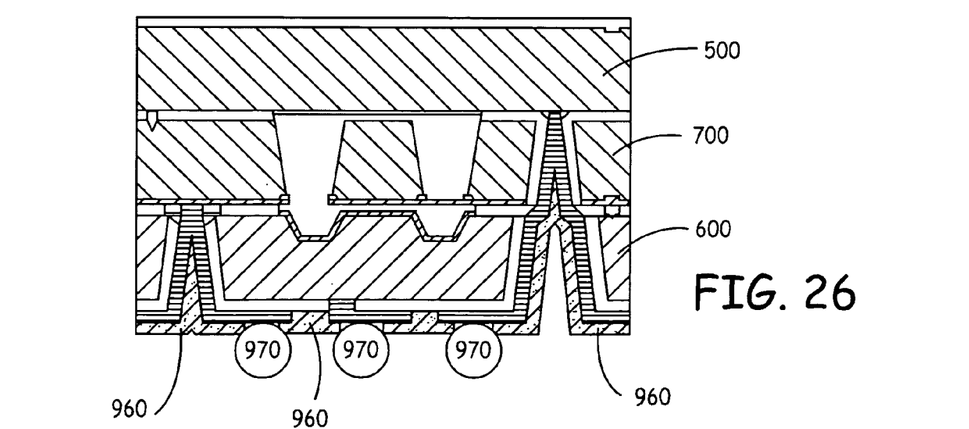

FIGS. 24–26 are cross-sectional views of a top cap, middle substrate, and a bottom cap coupled together in accordance with the present invention. The top cap and middle cap respectively corresponds to substrates 500 and 700 of FIGS. 22–23. The bottom cap corresponds to substrate 600 of FIGS. 12–15. Substrate 600 is aligned to substrate 700 using target fields 910. The target fields 910 are trenches formed in the surface of each substrate during previous wafer processing steps. In an embodiment of the wafer process, substrate 600 is coupled to substrate 700 in a fusion bond. Oxide layer 640 overlying substrate 600 is in contact with the surface of substrate 700. A heating step fuses oxide layer 640 to substrate 700 which permanently holds substrates 600 and 700 together.

Material is removed from substrate 600 in a thinning process. In an embodiment of the wafer process, substrate 600 is thinned to approximately 10 mils. An oxide layer 920 is formed on the surface of substrate 600. In an embodiment of the wafer process, oxide layer 920 is a passivation layer. Photoresist is formed overlying substrate 600 and patterned. The pattern exposes areas of oxide layer 920 corresponding to locations of vias through substrate 600. Exposed areas of oxide layer 920 are removed revealing underlying substrate 600. An etch is then performed on exposed substrate 600. In an embodiment of the wafer process, a TMAH etch is performed that etches through substrate 600 forming trenches 930. The etch is stopped upon reaching oxide layer 640 or oxide/nitride layer 625.

Referring to FIG. 25, photoresist is formed overlying oxide layer 940 and patterned. In the patterning process, photoresist is removed and trenches 930 are thoroughly cleaned out. Exposed areas of oxide layer 940 are then removed. In particular, contacts are being formed to couple to substrates 500, 600, and 700. Oxide/nitride layers are then removed in trenches 930 exposing portions of epitaxial layer 750 of substrate 700 and substrate 500. An implant is then performed to lower the contact resistance in coupling to substrates 500, 600, and 700. A metal layer 950 is then formed that overlies oxide layer 940 and contacts substrates 500, 600, and 700. Photoresist is then formed overlying metal layer 950 and patterned. Exposed portions of metal layer 950 are etched away. Metal layer 950 is patterned to define individual electrical contacts of the accelerometer. In an embodiment of the accelerometer, three electrical contact areas are defined corresponding to two terminals of two capacitors and a common terminal between the two capacitors. Moveable mass 850 is the common terminal of the two capacitors.

Referring to FIG. 26, a passivation layer 960 is formed overlying metal layer 950 and substrate 600. Passivation layer 960 protects the accelerometer from an external environment. Photoresist is then formed overlying passivation layer 960 and patterned. The pattern corresponds to electrical contact regions on substrate 600. Exposed areas of passivation layer 960 are removed exposing underlying metal layer 950. Solder bumps 970 are formed on the exposed areas of metal layer 950. As shown, three electrical contact regions are solder bumped that couple to substrate 500, substrate 600, and substrate 700. The electrical contact regions are approximately planar to one another and are accessible from the surface of substrate 600 allowing flip chip mounting to another substrate which minimizes the footprint of the accelerometer.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An accelerometer of an implantable medical device having a first terminal corresponding to a first plate of a first capacitor, a second terminal corresponding to a second plate of said first capacitor and a first plate of a second capacitor, and a third terminal corresponding to a second plate of said second capacitor, the accelerometer comprising:
   a first substrate coupled to the first terminal of the accelerometer, said first substrate being said first plate of the first capacitor;
   a second substrate bonded to said first substrate, said second substrate comprising:
      a moveable mass coupled to the second terminal of the accelerometer, said moveable mass being the second plate of the first capacitor and a first plate of the second capacitor;
      at least one S-shaped spring coupled to said moveable mass and said second substrate; and
   a third substrate bonded to said second substrate, said third substrate coupled to the third terminal of the accelerometer, said third substrate being the second plate of the second capacitor, wherein the moveable mass is prevented from moving in a direction that inelastically flexes the at least one S-shaped spring.

2. The accelerometer as recited in claim 1 wherein at least one over travel stop is formed on said moveable mass.

3. The accelerometer as recited in claim 1 wherein at least one over travel stop is formed on said second substrate.

4. The accelerometer as recited in claim 1 wherein said first, second, and third substrates comprise silicon.

5. The accelerometer as recited in claim 4 wherein a crystal orientation of said silicon is <100> and wherein said silicon is n-type.

6. The accelerometer as recited in 5 wherein said first substrate and said second substrate are fusion bonded together with an oxide layer and wherein said second substrate and said third substrate are fusion bonded together with an oxide layer.

7. The accelerometer as recited in claim 1 wherein electrical contact regions corresponding to the first, second, and third terminals of the accelerometer are formed on an exposed surface of said third substrate.

8. The accelerometer as recited in claim 7 wherein solder bumps are formed on said electrical contact regions of the accelerometer on said exposed surface of said third substrate allowing flip chip mounting of the accelerometer.

9. The accelerometer as recited in claim 1 wherein a first electrical contact region is formed on a major surface of said third substrate and wherein said first electrical contact region is coupled to said first substrate through an electrical contact that couples through said second and third substrates.

10. The accelerometer as recited in claim 9 wherein a second electrical contact region is formed on said major surface of said third substrate, the second electrical contact region coupling to said moveable mass and wherein said second electrical contact region is coupled to said moveable mass through an electrical contact that couples through said third substrate.

11. The accelerometer as recited in claim 10 wherein a third electrical contact region is formed on said major surface of said third substrate, said third electrical contact region coupling to said third substrate.

12. The accelerometer as recited in claim 1 wherein said moveable mass is suspended by S-shaped springs coupled to a single side of said moveable mass.

13. The accelerometer as recited in claim 1 wherein said moveable mass is suspended by S-shaped springs coupled to more than one side of said moveable mass.

14. An implantable medical device comprising:
a substrate having interconnect for coupling to circuitry of the implantable medical device; and
at least one accelerometer flip chip mounted to the substrate wherein the at least one accelerometer includes a moveable mass coupled to the at least one accelerometer by at least one spring and wherein movement of the moveable mass is limited to prevent inelastic flexing of the spring.

15. The implantable medical device as recited in claim 14 wherein the circuitry of the implantable medical device includes a pulse generator.

16. The implantable medical device as recited in claim 14 wherein the at least one accelerometer is a single axis accelerometer.

17. The implantable medical device as recited in claim 14 wherein the at least one accelerometer is a variable capacitance accelerometer.

18. The implantable medical device as recited in claim 17 wherein the at least one accelerometer comprises three substrates bonded together with the moveable mass being formed in a middle substrate, and wherein the implantable medical device further comprises at least one over travel stop to limit movement of the moveable mass.

19. A method of manufacturing a single axis accelerometer comprising the steps of:
providing a first semiconductor substrate;
forming a moveable mass in a second semiconductor substrate having a plurality of S-shaped springs coupled from the moveable mass to the second substrate;
releasing the moveable mass using a dry etch such that the moveable mass is limited from moving in any direction that inelastically flexes the plurality of S-shaped springs;
providing a third semiconductor substrate;
coupling the first semiconductor substrate to the second semiconductor substrate; and
coupling the third semiconductor substrate to the second semiconductor substrate.

20. The method of manufacturing a single axis accelerometer as recited in claim 19 further including a step of using n-type <100> silicon for the first, second, and third semiconductor substrate.

21. The method of manufacturing a single axis accelerometer as recited in claim 20 further including the steps of:
forming at least one p-well on a surface of the second semiconductor substrate;
forming an epitaxial layer overlying the surface of the second semiconductor substrate; and
using the at least one p-well as an etch stop in forming the moveable mass and the plurality of springs wherein the plurality of springs comprises material from the epitaxial layer.

22. The method of manufacturing a single axis accelerometer as recited in claim 21 further including the steps of:
forming a non-conductive layer on a surface of the first semiconductor substrate to prevent a short condition when the moveable mass contacts the first semiconductor substrate; and
forming a non-conductive layer on a surface of the third semiconductor substrate to prevent a short condition when the moveable mass contacts the third semiconductor substrate.

23. The method of manufacturing a single axis accelerometer as recited in claim 19 further including the steps of:
forming at least one over travel stop on the moveable mass; and
using a dry etch to etch a space between the at least one over travel stop and the second semiconductor substrate wherein spacing between the at least one over travel stop and the second semiconductor substrate limits movement of the moveable mass such that the plurality of springs do not inelastically flex.

24. The method of manufacturing a single axis accelerometer as recited in claim 19 further including the steps of:
forming at least one over travel stop on the second semiconductor substrate; and
using a dry etch to etch a space between the at least one over travel stop and the moveable mass wherein spacing between the at least one over travel stop and the second semiconductor substrate limits movement of the moveable mass such that the plurality of springs do not inelastically flex.

25. The method of manufacturing a single axis accelerometer as recited in claim 19 further including a step of forming the plurality of springs on single side of the moveable mass.

26. The method of manufacturing a single axis accelerometer as recited in claim 19 further including a step of forming the plurality of springs on more than one side of the moveable mass.

27. The method of manufacturing a single axis accelerometer as recited in claim 19 further including the steps of:
- forming a first via through the third semiconductor substrate and the second semiconductor substrate to expose the first semiconductor substrate;
- forming a first electrical contact region on a surface of the third semiconductor substrate that couples to the first substrate through the first via;
- forming a second via through the third semiconductor substrate to expose the second semiconductor substrate;
- forming a second electrical contact region on the surface of the third semiconductor substrate that couples to the second semiconductor substrate through the second via; and
- forming a third electrical contact region on the surface of the third semiconductor substrate that couples to the third semiconductor substrate.

28. The method of manufacturing a single axis accelerometer as recited in claim 27 further including a step of solder bumping the first, second, and third electrical contact regions to allow coupling of the single axis accelerometer to another substrate.

29. The method of manufacturing a single axis accelerometer as recited in claim 19 wherein the step of coupling the first semiconductor substrate to the second semiconductor substrate further includes the steps of:
- using oxide fusion bonding to couple a major surface of the first semiconductor substrate to a first major surface of the second semiconductor substrate wherein the major surface of the first substrate is spaced a first predetermined distance from the moveable mass; and
- using oxide fusion bonding to couple a major surface of the third semiconductor substrate to a second major surface of the second semiconductor substrate wherein the major surface of the third semiconductor substrate is a second predetermined distance from the moveable mass.

* * * * *